United States Patent
Noh et al.

(10) Patent No.: US 11,800,998 B2
(45) Date of Patent: Oct. 31, 2023

(54) PERSONAL AUTHENTICATION DEVICE BASED ON AUDITORY BRAINSTEM RESPONSE SIGNAL AND METHOD THEREOF

(71) Applicant: ELECTRONICS AND TELECOMMUNICATIONS RESEARCH INSTITUTE, Daejeon (KR)

(72) Inventors: Hyung Wook Noh, Sejong (KR); Joo Yong Sim, Daejeon (KR); Chang-Geun Ahn, Sejong (KR); Bong Kyu Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 530 days.

(21) Appl. No.: 16/687,366

(22) Filed: Nov. 18, 2019

(65) Prior Publication Data

US 2020/0159902 A1 May 21, 2020

(30) Foreign Application Priority Data

Nov. 19, 2018 (KR) .......................... 10-2018-0143034

(51) Int. Cl.
*A61B 5/117* (2016.01)
*A61B 5/38* (2021.01)
(Continued)

(52) U.S. Cl.
CPC ................ *A61B 5/117* (2013.01); *A61B 5/12* (2013.01); *A61B 5/38* (2021.01); *A61B 5/7264* (2013.01);
(Continued)

(58) Field of Classification Search
CPC .. A61B 5/117; A61B 5/38; A61B 5/12; A61B 5/7264; G06F 3/015; G06F 21/32; G06F 21/34
(Continued)

(56) References Cited

U.S. PATENT DOCUMENTS

| 7,529,379 | B2 | 5/2009 | Zurek et al. |
| 10,154,333 | B2 | 12/2018 | Campbell et al. |

(Continued)

FOREIGN PATENT DOCUMENTS

| CN | 105389494 A | * 3/2016 | ............ G06F 21/32 |
| KR | 101607432 B1 | 3/2016 | |

(Continued)

OTHER PUBLICATIONS

Sung Hwa Hong et al., "Overview of Evoked Response Audiometry", 2009, Korean Journal of Audiology & Otology 2009;13:1-11, ISSN 1226-6507.
Neil J. Grabham et al., "An Evaluation of Otoacoustic Emissions as a Biometric", IEEE Transactions on Information Forensics and Security, vol. 8, No. 1, Jan. 2013.

*Primary Examiner* — Kwin Xie (57) ABSTRACT

Provided is a personal authentication device based on an auditory brainstem response signal. The personal authentication device includes a signal generator, a signal acquirer, and a signal processor. The signal generator may output an auditory stimulus to an ear of a user, using a sound generator. The signal acquirer may acquire a first reference potential corresponding to a first interval, from a first electrode in close contact with the other ear of the user, and acquire a first evoked potential corresponding to the first interval from a second electrode in close contact with the ear, based on the first reference potential. The signal processor may generate a first auditory brainstem response signal, based on the first reference potential and the first evoked potential, generate authentication data for the user from the first auditory (Continued)

brainstem response signal, and compare the authentication data with registration data to authenticate the user.

20 Claims, 7 Drawing Sheets

(51) Int. Cl.
  *A61B 5/12* (2006.01)
  *A61B 5/00* (2006.01)
  *G06F 3/01* (2006.01)
  *G06F 21/32* (2013.01)
  *G06F 21/34* (2013.01)

(52) U.S. Cl.
  CPC .............. *G06F 3/015* (2013.01); *G06F 21/32* (2013.01); *G06F 21/34* (2013.01)

(58) Field of Classification Search
  USPC ........................................................ 600/559
  See application file for complete search history.

(56) References Cited

U.S. PATENT DOCUMENTS

| | | |
|---|---|---|
| 2012/0032781 A1 | 2/2012 | Moon et al. |
| 2012/0200601 A1* | 8/2012 | Osterhout ............ G02B 27/017 345/633 |
| 2013/0063550 A1* | 3/2013 | Ritchey ................ A61B 5/7264 345/207 |
| 2016/0320840 A1* | 11/2016 | Hwang ................ H04R 1/1041 |
| 2018/0157814 A1 | 6/2018 | Yoo et al. |

FOREIGN PATENT DOCUMENTS

| | | | |
|---|---|---|---|
| KR | 101630398 B1 | 6/2016 | |
| KR | 20170026881 A | 3/2017 | |
| KR | 20180044964 A | 5/2018 | |
| WO | WO-2016110804 A1 * | 7/2016 | ............... A61B 3/16 |

* cited by examiner

Right Ear

FIG. 3

Left Ear

PERSONAL AUTHENTICATION DEVICE BASED ON AUDITORY BRAINSTEM RESPONSE SIGNAL AND METHOD THEREOF

CROSS-REFERENCE TO RELATED APPLICATIONS

This U.S. non-provisional patent application claims priority under 35 U.S.C. § 119 to Korean Patent Application No. 10-2018-0143034, filed on Nov. 19, 2018, in Korean Intellectual Property Office, the entire contents of which are incorporated herein by reference.

BACKGROUND

Embodiments relate to a personal authentication device and a personal authentication method, and more particularly, relate to a personal authentication device and a personal authentication method, based on a auditory brainstem response signal.

A personal authentication using biometric information is used for security, instead of a conventional personal authentication using passwords, security keys, etc. Among the biometric information, biometric information based on an image, such as fingerprints, faces, and irises, is generally used for the personal authentication. Recently, image-based biometric information is increasingly used for hacking, replication, and theft, and alternative technologies and anti-theft technologies are being developed.

Unlike the biometric information based on the image, the biometric information using frequency domain transfer characteristics is relatively difficult to replicate. Therefore, the biometric information using the frequency domain transfer characteristics may be usefully used for the personal authentication. Among the biometric information using the frequency domain transfer characteristics, an auditory brainstem response (ABR) signal may be used for the personal authentication.

SUMMARY

Embodiments of the inventive concept provide a personal authentication device and a personal authentication method, based on an auditory brainstem response signal.

According to an exemplary embodiment, a personal authentication device may include a signal generator, a signal acquirer, and a signal processor. The signal generator may output an auditory stimulus to an ear of a user, using a sound generator. The signal acquirer may acquire a first reference potential corresponding to a first interval from a first time at which the auditory stimulus is input to the ear of the user to a second time, from a first electrode in close contact with the other ear of the user, and acquire a first evoked potential corresponding to the first interval from a second electrode in close contact with the ear of the user, based on the first reference potential. The signal processor may generate a first auditory brainstem response signal, based on the first reference potential and the first evoked potential, generate authentication data for the user from the first auditory brainstem response signal, and compare the authentication data with registration data to authenticate the user.

According to an exemplary embodiment, a personal authentication method includes outputting an auditory stimulus for a registration of a user to an ear of the user, using a sound generator, generating registration data for the user, using a first evoked potential corresponding to a first interval from a first time at which the auditory stimulus is input to the ear of the user to a second time, from an electrode in close contact with the ear of the user, outputting the auditory stimulus for an authentication of the user to the ear of the user, using the sound generator, generating authentication data for the user, using a second evoked potential corresponding to a second interval from a third time at which the auditory stimulus is input to the ear of the user to a fourth time, from the electrode, and comparing the registration data with the authentication data to authenticate the user.

BRIEF DESCRIPTION OF THE DRAWINGS

Fearues will become apparent to those of skill in the art by describing in detail exemplary embodiments with reference to the attached drawings in which.

DETAILED DESCRIPTION

Embodiments of the inventive concept will be described below in more detail with reference to the accompanying drawings. In the following descriptions, details such as detailed configurations and structures are provided merely to assist in an overall understanding of embodiments of the inventive concept. Modifications of the embodiments described herein can be made by those skilled in the art without departing from the spirit and scope of the inventive concept.

Figure 1:
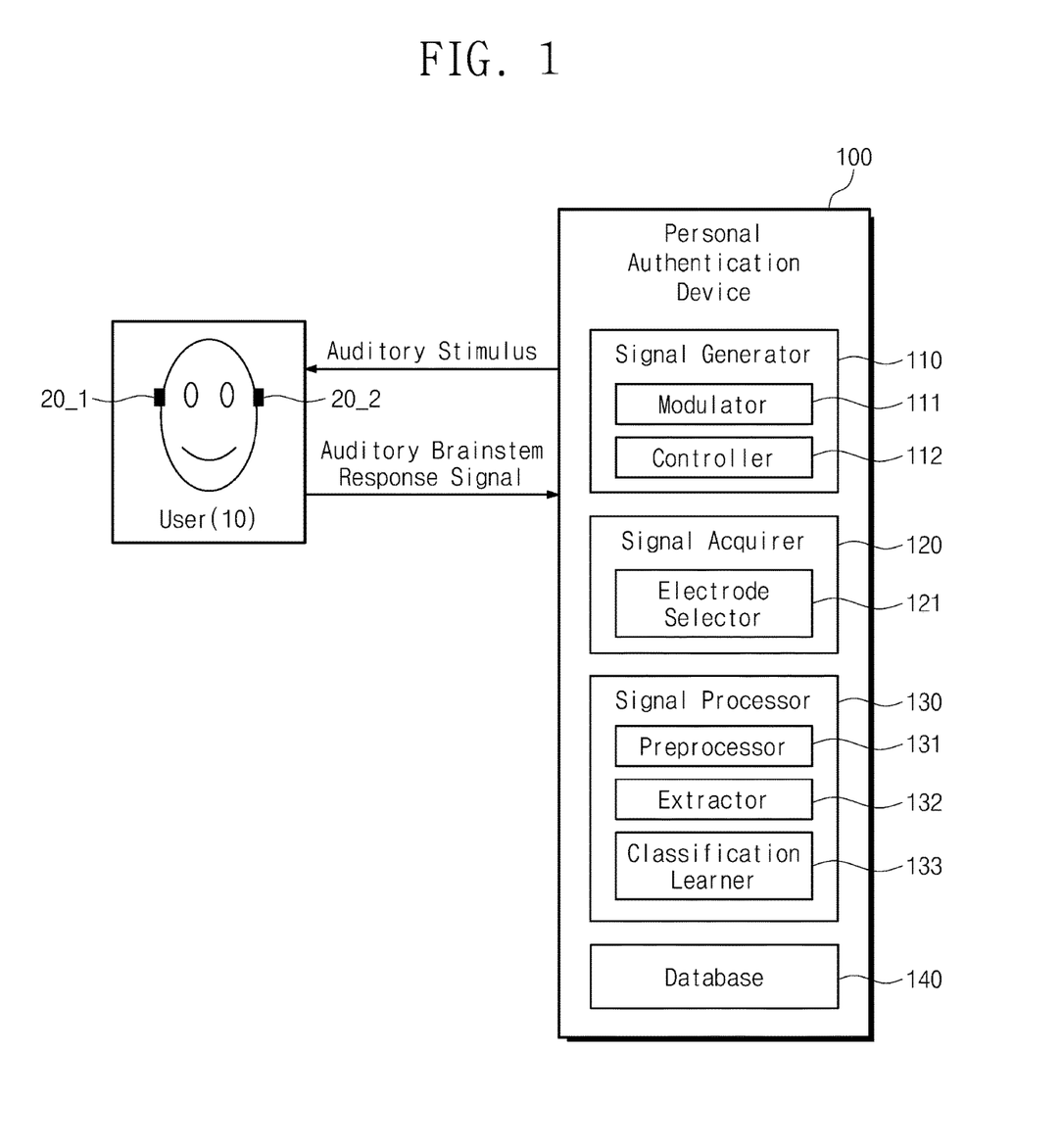
FIG. 1 illustrates a personal authentication device based on an auditory brainstem response signal and a user according to an example embodiment.

FIG. 1 illustrates a personal authentication device based on an auditory brainstem response signal and a user according to an example embodiment. In the following, a left side and a right side for identifying each of ears are based on a user 10.

The personal authentication device 100 may include a signal generator 110, a signal acquirer 120, a signal processor 130, and a database 140. The signal generator 110 may generate any kind of sound stimulus that may be used as an auditory stimulus including a click, a tone burst, or repetitive stimulus sound having single frequency characteristic. The auditory stimulus may also be referred to as an input stimulus signal or an auditory stimulus signal to the user 10. The signal generator 110 may output the auditory stimulus to the left or right ear of the user 10 using first and second sound generators 20_1 and 20_2. The first and second sound generators 20_1 and 20_2 may be separated from the signal generator 110. Alternatively, the first and second sound generators 20_1 and 20_2 may be included in the signal generator 110.

The signal generator 110 may supply the auditory stimulus to the left or right ear of the user 10, using the first or second sound generator 20_1 or 20_2. The signal generator 110 may separately provide the auditory stimulus to both ears of the user 10 by the first and second sound generators 20_1 and 20_2. When the auditory stimulus is output to an ear of the user 10 through the first sound generator 20_1, the signal generator 110 may not output the auditory stimulus to the other ear of the user 10, using the second sound generator 20_2. In addition, when the auditory stimulus is output to the other ear of the user 10 through the second sound generator 20_2, the signal generator 110 may not output the auditory stimulus to the ear of the user 10, using the first sound generator 20_1.

The signal generator 110 may repeatedly output the auditory stimulus to the left or right ear of the user 10, using the first and second sound generators 20_1 and 20_2. The signal generator 110 may repeatedly output auditory stimuli to the left ear or right ear through the first and second sound generators 20_1 and 20_2 for a unit time. For example, the unit time may be within 1000 ms. The signal generator 110 may repeatedly output the auditory stimuli to the left ear or right ear through the first and second sound generators 20_1 and 20_2 for the unit time by a predetermined number of times. For example, the predetermined number of times may be 1000 or more times. An auditory brainstem responses (ABRs) generated from the user 10 that receives the input stimulus signal for the first time or several times may be relatively low in consistency or convergence. When the consistency or the convergence of the auditory brainstem response signals is relatively low, the auditory brainstem response signals may not be suitable for authenticating the user 10. Thus, the auditory stimuli or the input stimulus signals need to be repeatedly provided to the user 10. The auditory brainstem response signal will be described in more detail with reference to FIG. 4.

The signal generator 110 may include a modulator 111 and a controller 112. The modulator 111 may modulate and determine a waveform, a frequency, and an intensity of the auditory stimulus. The modulator 111 may modulate and determine the waveform, the frequency, and the intensity of the auditory stimulus, based on predefined conditions. The auditory stimulus having the waveform, the frequency, and the intensity that are determined by the modulator 111 may be provided to the user 10 through the first and second sound generators 20_1 and 20_2. The modulator 111 may modulate the waveform, the frequency, and the intensity of the auditory stimulus based on various conditions. The auditory stimuli having the waveform, the frequency, and the intensity that are determined by modulator 111 may be different depending on conditions.

For example, the modulator 111 may modulate the waveform, the frequency, and the intensity of a first auditory stimulus, based on a first condition, and modulate the waveform, the frequency, and the intensity of a second auditory stimulus, based on a second condition. The first auditory stimulus based on the first condition may be different from the second auditory stimulus based on the second condition. The modulator 111 may determine the waveform of the auditory stimulus as any one of various waveforms such as triangular, square, sine, pulse, click, sawtooth, ramp, chirp, tone pip, and tone burst. The frequency determined by the modulator 111 may be included in an audible frequency (20 Hz to 20,000 Hz) or a range other than the audible frequency. The intensity of the auditory stimulus may be referred to as a sound intensity or a sound pressure level.

The controller 112 may control the first and second sound generators 20_1 and 20_2 such that the auditory stimulus is output through the first and second sound generators 20_1 and 20_2. The controller 112 may control one of the first and second sound generators 20_1 and 20_2 such that the auditory stimulus is output through one of the first and second sound generators 20_1 and 20_2, based on a selection of the user 10. The controller 112 may control the first and second sound generators 20_1 and 20_2 to supply the auditory stimulus in a direction desired by the user 10. The auditory stimulus may be provided to the ear that is selected by the user 10. Alternatively, the controller 112 may optionally allow the auditory stimulus to be output through one of the first and second sound generators 20_1 and 20_2. The first and second sound generators 20_1 and 20_2 may optionally provide the auditory stimulus to either the left ear or the right ear by the controller 112. An evoked potential may occur from the user 10 that receives the auditory stimulus. The evoked potential may be generated in each of the left and right ears.

The signal acquirer 120 may acquire the evoked potential from the user 10. Alternatively, the signal acquirer 120 may directly receive the auditory brainstem response signal from the user 10. The signal acquirer 120 may alternately acquire a plurality of auditory brainstem response signals from both ears from the user 10 through a plurality of electrodes. For example, the number of the plurality of electrodes may be equal to the number of ears of the user 10. The plurality of electrodes may be separated from the signal acquirer 120. Alternatively, the plurality of electrodes may be included in the signal acquirer 120. The evoked potential may be measured through a measuring electrode, based on a reference potential that are measured by a reference electrode. The plurality of electrodes may be positioned in the left ear canal or the right ear canal of the user 10. The plurality of electrodes may contact an inner face of the left ear canal or right ear canal. Alternatively, the plurality of electrodes may be attached to a forehead, a mastoid, and a calvaria of the user 10.

The signal acquirer 120 may include an electrode selector 121. The electrode selector 121 may select the measuring electrode and the reference electrode among the plurality of electrodes. The electrode selector 121 may be synchronized with the controller 112 and may select the measuring electrode and the reference electrode, based on a selection of the controller 112. For example, the controller 112 may select an electrode that is attached to the ear selected by the user 10 as the measuring electrode and select an electrode that is attached to the ear not selected by the user 10 as the reference electrode. The signal acquirer 120 may acquire the evoked potential and a reference potential from the measuring electrode and the reference electrode. The signal acquirer 120 may acquire the evoked potential, based on the reference potential.

The signal processor 130 may authenticate the user 10, based on the auditory brainstem response signal. In more detail, the signal processor 130 may generate the auditory brainstem response signal, based on the evoked potential that is provided from the signal acquirer 120. Alternatively, one of the signal acquirer 120 and the signal processor 130 may generate the auditory brainstem response signal, based on the evoked potential. The signal processor 130 may extract features for the user 10, based on the auditory brainstem response signal and generate authentication data and registration data for the user 10, based on the extracted features. The signal processor 130 may include a preprocessor 131, an extractor 132, and a classification learner 133.

The preprocessor 131 may preprocess the evoked potentials acquired by the signal acquirer 120 to generate first and second auditory brainstem response signals. The evoked potential and the reference potential may be transmitted from the plurality of electrodes to the preprocessor 131. The evoked potential and the reference potential may be transmitted in electrical signals. The preprocessor 131 may take an ensemble average of the evoked potentials that are repeatedly measured. The preprocessor 131 may generate the auditory brainstem response signal, based on the ensemble averaged evoked potentials. The preprocessor 131 may amplify the received evoked potentials. The preprocessor 131 may remove noise of the received evoked potentials. The preprocessor 131 may convert the amplified or filtered evoked potentials into digital signals. For example, the preprocessor 131 may include an amplifier, a filter, an analog-to-digital converter (ADC), etc. for preprocessing the received evoked potentials.

The extractor 132 may extract features or characteristics of the auditory brainstem response signals and may generate the authentication data and the registration data for the user 10. The authentication data extracted by the extractor 132 may be unique information for each individual. The registration data is similar to the authentication data, but may be data that are generated by initially registering the user 10 on the personal authentication device 100. The registration data may be stored in the database 140 described later. The authentication data and the registration data may be data corresponding to the user 10. The extractor 132 may extract the authentication data or characteristic data and the registration data of the user 10, based on the auditory brainstem response signals. The authentication data and registration data may include features of the auditory brainstem response signals. For example, the characteristics of the auditory brainstem response signals may indicate changes in a voltage, a current, an amplitude, a magnitude, a frequency, a phase, etc. over time. The extractor 132 may extract the authentication data and the registration data periodically or aperiodically.

For example, the extractor 132 may extract first authentication data for a first user and may extract second authentication data for a second user. The first authentication data may be different from the second authentication data. Therefore, the personal authentication device 100 may distinguish the first user from the second user, based on first registration data, second registration data, the first authentication data, and the second authentication data.

The classification learner 133 may register the user 10 or authenticate the user 10. In an authentication process, the classification learner 133 may calculate a score of the user 10, based on authentication data of the user 10. The personal authentication device 100 may authenticate the user 10, based on the score of the user 10. The classification learner 133 may store a reference score and the score of the user, and provide an authentication result to the user 10 by comparing the score of the user with the reference score. In a registration process, the classification learner 133 may store the registration data of the user 10 in the database 140 described later. When the registration process for the user 10 is performed in advance, the classification learner 133 may not repeatedly perform the registration process for the user 10.

The classification learner 133 may classify the auditory brainstem response signals, based on the extraction result of the extractor 132 and cognitive information. For example, at least one user may be registered on the personal authentication device 100. The classification learner 133 may classify the auditory brainstem response signals depending on registered users. The classification learner 133 may classify the auditory brainstem response signals, based on the characteristics of the auditory brainstem response signals such as the voltage, the current, the amplitude, the magnitude, the frequency, and the phase. The classification learner 133 may classify the auditory brainstem response signals, based on the auditory stimulus received by the user 10. The classification learner 133 may classify the auditory brainstem response signals, based on conditions other than the above-described exemplary conditions.

The database 140 may store the extraction result of the extractor 132 and the classification result of the classification learner 133. The database 140 may store conditions for modulating the auditory stimuli. The database 140 may store the authentication data, the registration data, and the score of the user, which is calculated for providing the user 10 with the authentication result of the user 10. The auditory brainstem response signal of the user 10 may be sequentially processed by the extractor 132 and the classification learner 133 of the signal processor 130, and information (i.e., the extraction result and the classification result) of the processed auditory brainstem response signal may be stored in the database 140. The signal processor 130 may authenticate the user 10, based on the registration data stored in the database 140.

In an embodiment, the database 140 may be implemented using various storage devices such as a hard disk drive (HDD), a solid state drive (SSD), a server, a RAM, a memory, etc. capable of storing information of a digital type. The database 140 may be implemented separately from the signal processor 130 in hardware. Alternatively, the database 140 may be implemented within the signal processor 130.

Figure 2:
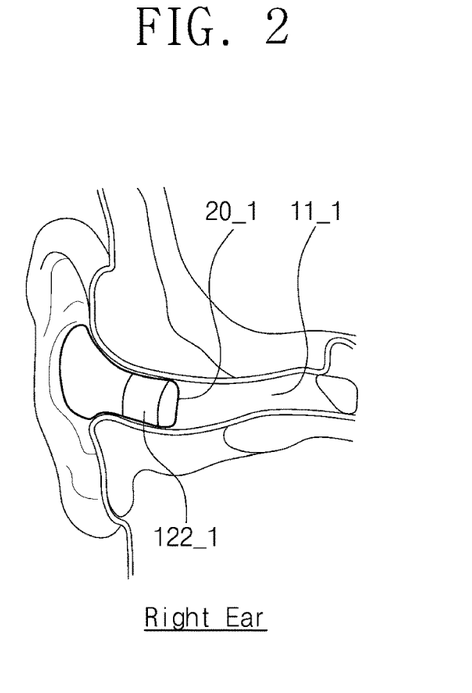
FIGS. 2 and 3 illustrate both ears of a user using a personal authentication device according to an example embodiment.
Figure 3:
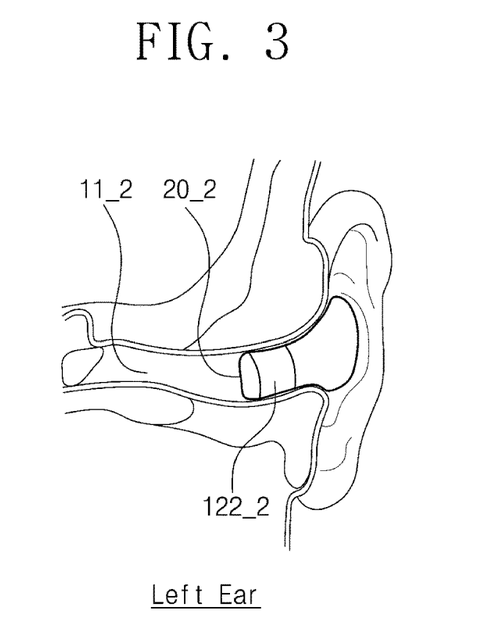

FIGS. 2 and 3 illustrate both ears of a user using a personal authentication device according to an example embodiment. FIGS. 2 and 3 will be described together with FIG. 1. In the following, the left and right sides for identifying each of ears are based on the user.

The first and second sound generators 20_1 and 20_2 may be earphone-shaped. The first and second sound generators 20_1 and 20_2 may be inserted into ear canals 11_1 and 11_2 of both ears, respectively. Referring to FIGS. 2 and 3, the first sound generator 20_1 may be inserted into the ear canal 11_1 of the right ear and the second sound generator 20_2 may be inserted into the ear canal 11_2 of the left ear.

First and second electrodes 122_1 and 122_2 may be a ring-shaped or a loop-shaped. The first and second electrodes 122_1 and 122_2 may be combined with the first and second sound generators 20_1 and 20_2, respectively. The first and second electrodes 122_1 and 122_2 may surround surfaces of the first and second sound generators 20_1 and 20_2, respectively or may be attached to the first and second sound generators 20_1 and 20_2, respectively. In detail, the first and second electrodes 122_1 and 122_2 may be attached to the surfaces of the first and second sound generators 20_1 and 20_2, respectively. The first and second electrodes 122_1 and 122_2 may be positioned in the ear canals 11_1 and 11_2 of both ears, respectively. For example, the first electrode 122_1 may contact an inner surface of the ear canal 11_1 of the right ear and the second electrode 122_2 may contact an inner surface of the ear canal 11_2 of the left ear.

The auditory stimuli may be alternately output from the first and second sound generators 20_1 and 20_2. The controller 112 may alternately select the first and second sound generators 20_1 and 20_2, and the first and second sound generators 20_1 and 20_2 selected by the controller 112 may repeatedly output the auditory stimuli.

The electrode selector 121 may be synchronized with the controller 112. The electrode selector 121 may select the measuring electrode and the reference electrode, based on a selection of the controller 112. For example, when the controller 112 selects the first sound generator 20_1, the electrode selector 121 may select the first electrode 122_1, and when the controller 112 selects the second sound generator 20_2, the electrode selector 121 may select the second electrode 122_2.

In an embodiment, when the auditory stimuli are applied to the right ear and the electrode of the right ear receives auditory brainstem response signals, the electrode of the left ear may be the reference electrode. The electrode of the right ear may receive the auditory brainstem response signals, based on the signals received by the electrode of the left ear. In contrast, when the auditory stimuli are applied to the left ear and the electrode of the left ear receives the auditory brainstem response signals, the electrode of the right ear may be the reference electrode. The electrode of the left ear may receive the auditory brainstem response signals, based on the signals received by the electrode of the right ear. The auditory brainstem response signal will be described in more detail in FIG. 4.

In an embodiment, the signal generator 110 may output the auditory stimulus to the ear of the user 10, using the first sound generator 20_1. The signal acquirer 120 may acquire the first reference potential corresponding to a unit interval from the first electrode 122_1 in close contact with the other ear of the user 10, and acquire the first evoked potential corresponding to the unit interval from the second electrode 122_2 in close contact with the ear of the user 10, based on the first reference potential. The signal acquirer 120 may control a width of the unit interval. For example, the unit interval may be an interval from a start time at which the auditory stimulus is input to the ear of the user 10 to 10 ms. The signal processor 130 may generate the first auditory brainstem response signal, based on the first reference potential and the first evoked potential.

In addition, the signal generator 110 may output the auditory stimulus to the other ear of the user 10, using the second sound generator 20_2. The signal generator 110 may generate the second auditory brainstem response signal, using the second sound generator 20_2, in a manner similar to that of generating the first auditory brainstem response signal. The extractor 132 may generate the authentication data from the first and second auditory brainstem response signals. The classification learner 133 may authenticate the user 10 by comparing the authentication data with the registration data.

In another embodiment, the signal generator 110 may repeatedly output the auditory stimulus to the ear of the user 10, using the first sound generator 20_1. The signal acquirer 120 may repeatedly acquire third reference potentials corresponding to a unit interval from the first electrode 122_1 in close contact with the other ear of the user 10, and repeatedly acquire third evoked potentials corresponding to the unit interval from the second electrode 122_2 in close contact with the ear of the user 10, based on the third reference potentials. In this case, the unit interval may be an interval from a start time at which the auditory stimulus is repeatedly input to the ear of the user 10 to 10 ms. The preprocessor 131 may preprocess the third reference potentials and the third evoked potentials, and calculate averages of the preprocessed third reference potentials and the third evoked potentials. The preprocessor 131 may generate a third auditory brainstem response signal, using an average of the third reference potentials and an average of the third evoked potentials.

In addition, the signal generator 110 may repeatedly output the auditory stimulus to the other ear of the user 10, using the second sound generator 20_2. The signal generator 110 may generate a fourth auditory brainstem response signal, using the second sound generator 20_2, in a manner similar to that of generating the third auditory brainstem response signal. The extractor 132 may generate the authentication data from the third and fourth auditory brainstem response signals. The classification learner 133 may authenticate the user 10 by comparing the authentication data with the registration data.

Figure 4:
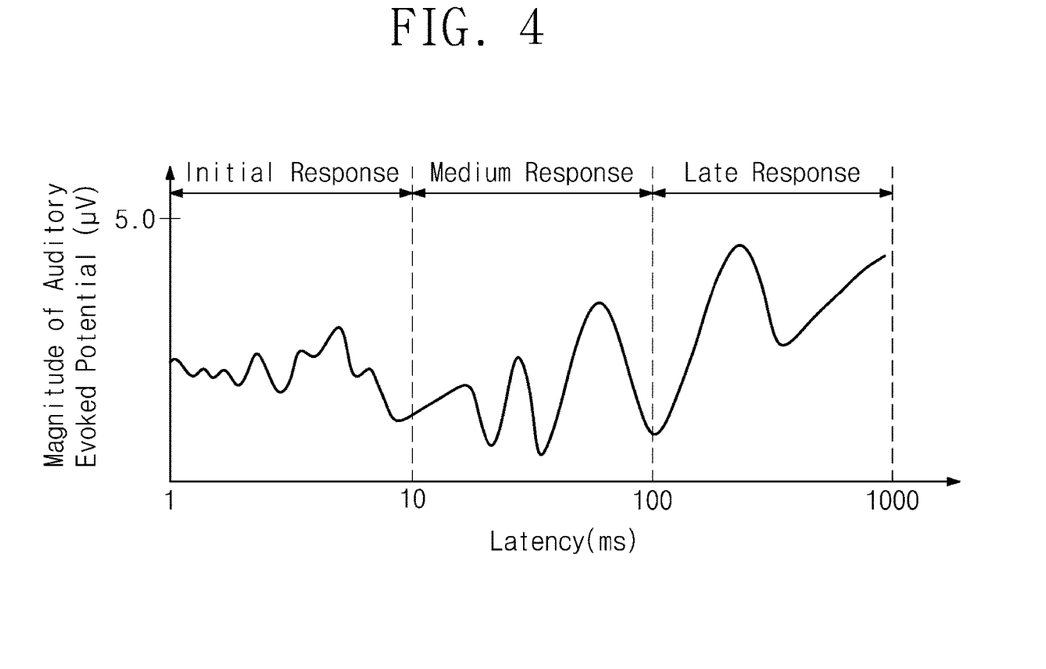
FIG. 4 illustrates magnitudes of an auditory evoked potential over a latency.

FIG. 4 illustrates magnitudes of an auditory evoked potential over a latency. The auditory evoked potential is an electrical signal that arises from an auditory evoked response.

When the auditory stimulus is applied to the ear, a stimulus is transferred along an auditory organ, an electrical nerve stimulus may occur in hair cells of a cochlea from a transferring process. The electrical nerve stimulus may be transferred to neurons in a bundle of auditory nerves. The action potential of the electrical nerve stimulus detected from the neurons is called the auditory evoked potential (AEP).

The auditory evoked potential is different from a brainwave and an electroencephalography (EEG). In a frequency domain, the brainwave is generally detected in a region of 0 Hz to 30 Hz. However, a signal of the auditory evoked potential is detected in a region of 100 Hz to 4 kHz. In other words, a bandwidth of the brainwave in the frequency domain is different from a bandwidth of the signal of the auditory evoked potential.

In general, electrodes for measuring the evoked potentials depending on the auditory evoked response may be attached to the forehead, the mastoid, and the calvaria. A ground electrode may be attached to the forehead. In an example embodiment, the electrodes may be attached to the inner surface of the ear canal.

Referring to FIG. 4, the auditory evoked response may be classified into an initial response, a medium response, and a late response, based on an interval of a latency. The latency is measured from a start time of the auditory stimulus. The initial response, the medium response, and late response of the auditory evoked response may be divided, based on the intervals of the latency that classify peaks of the auditory evoked potential graph. For example, the initial response may be an interval from a time when the latency of the auditory evoked response is 0 ms to a time when the latency is 10 ms, the medium response may be an interval from a time when the latency of the auditory evoked response is 10 ms to a time when the latency is 100 ms, the late response may be an interval from a time when the latency of the auditory evoked response is 100 ms to a time when the latency is 750 ms. The initial response is also called the auditory brainstem response. The auditory brainstem response signal may be generated based on the evoked potential signal that is detected from the auditory brainstem response.

The auditory brainstem response signal may be generated based on a result of repeatedly acquiring the evoked potentials depending on the auditory evoked response. The evoked potentials may be measured by synchronizing with auditory stimuli that are applied to the ear for the unit time.

The auditory brainstem response signal may be generated by taking an ensemble average of repeatedly measured evoked potentials.

The features of the auditory brainstem response signal, such as the frequency, the amplitude, the phase, etc. may be changed based on the auditory stimulus. An individual person may have the features of the unique auditory brainstem response signal. The features of the unique auditory brainstem response signal may be used for personal authentication.

Figure 5:
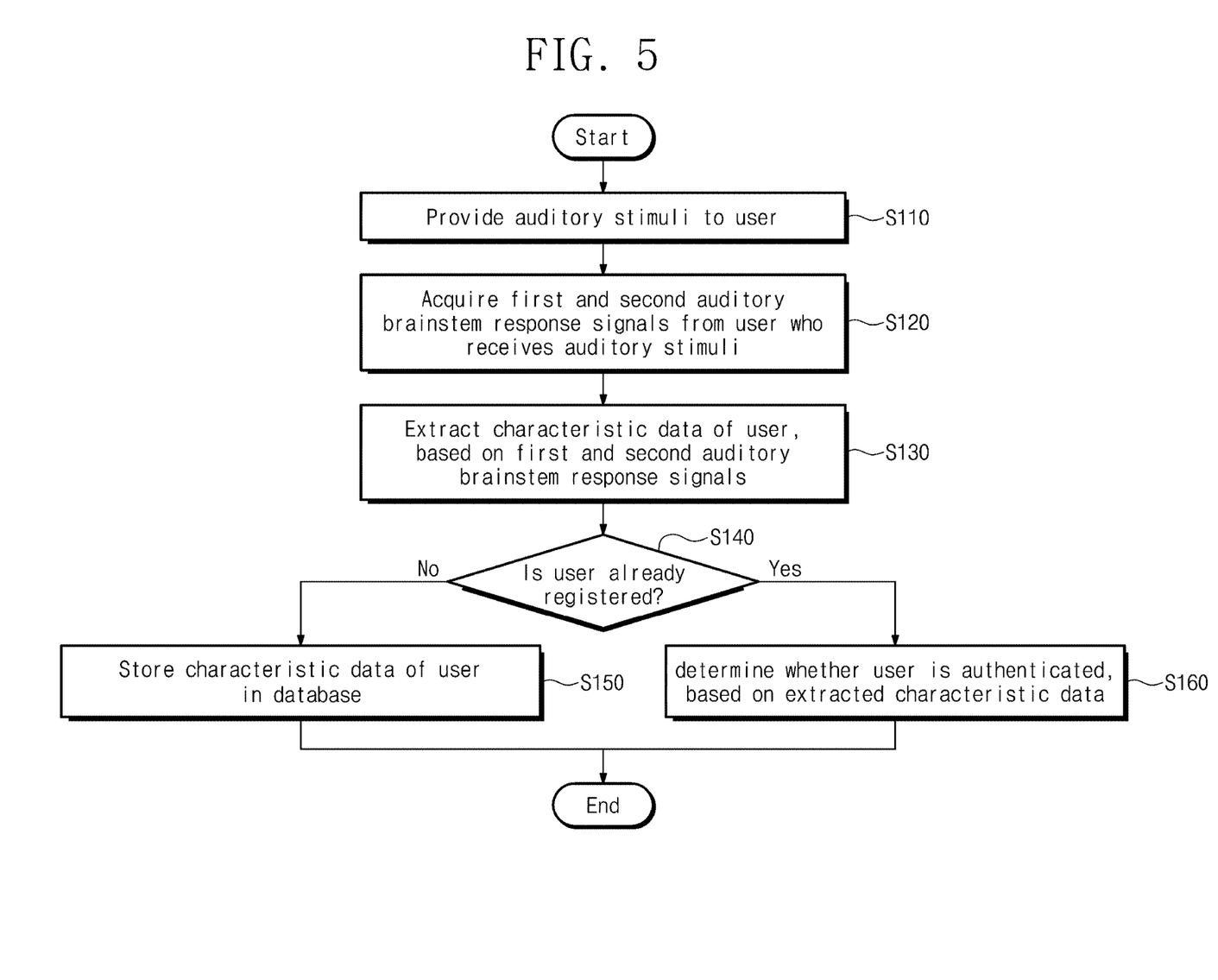
FIG. 5 illustrates a flowchart describing a personal authentication method based on an auditory brainstem response signal according to an example embodiment.

FIG. 5 illustrates a flowchart describing a personal authentication method based on an auditory brainstem response signal according to an example embodiment. FIG. 5 will be described with FIG. 1

In operation S110, the signal generator 110 may provide the auditory stimuli to the user 10. The auditory stimuli may be generated by the signal generator 110. The auditory stimulus for registration of the user 10 may be the same as the auditory stimulus for authentication of the user 10. The signal generator 110 may output the auditory stimulus for registration of the user 10 to the ears of the user 10, using the first and second sound generators 20_1 and 20_2. In addition, the signal generator 110 may output the auditory stimulus for authentication of the user 10 to the ears of the user 10, using the first and second sound generators 20_1 and 20_2. Operation S110 will be described in more detail in FIG. 6.

In operation S120, the personal authentication device 100 may acquire the plurality of auditory brainstem response signals from the user 10 who receives the auditory stimuli through the signal acquirer 120 and the signal processor 130. The signal acquirer 120 may acquire the evoked potential and the reference potential from the user 10, and the signal processor 130 may generate the auditory brainstem response signals by using the evoked potential and the reference potential. The plurality of auditory brainstem response signals may include the first and second auditory brainstem response signals. Operation S120 will be described in more detail in FIG. 7.

In operation S130, the extractor 132 may extract the characteristic data or the authentication data and the registration data of the user, based on the first and second auditory brainstem response signals. The signal processor 130 may generate the registration data for the user 10, using the evoked potential corresponding to the unit interval from the electrode in close contact with the ear of the user 10. The unit interval may be an interval from the start time at which the auditory stimulus is input to the ear of the user 10 to 10 ms.

In operation S140, the classification learner 133 may determine whether the user 10 is registered on the personal authentication device 100. When the user is registered, operation S160 may proceed. Otherwise, operation S150 may proceed. Whether the user 10 is registered may be determined based on whether the registration data of the user 10 is stored in the database 140. When the registration data of the user 10 is stored in the database 140, the classification learner 133 may determine that the user 10 is registered. When the registration data of the user 10 is not stored in the database 140, the classification learner 133 may determine that the user 10 is not registered.

In operation S150, the classification learner 133 may store the registration data extracted in operation S130 in the database 140. The personal authentication device 100 may authenticate the user 10 by comparing the registration data with the authentication data. In the authentication process, the registration data may be invoked from the database 140 and used by the classification learner 133.

In operation S160, the classification learner 133 may determine whether the user is authenticated, based on the characteristic data or the authentication data extracted in operation S130. The signal processor 130 may authenticate the user by comparing the registration data with the authentication data. Operation S160 will be described in more detail in FIG. 8.

Figure 6:
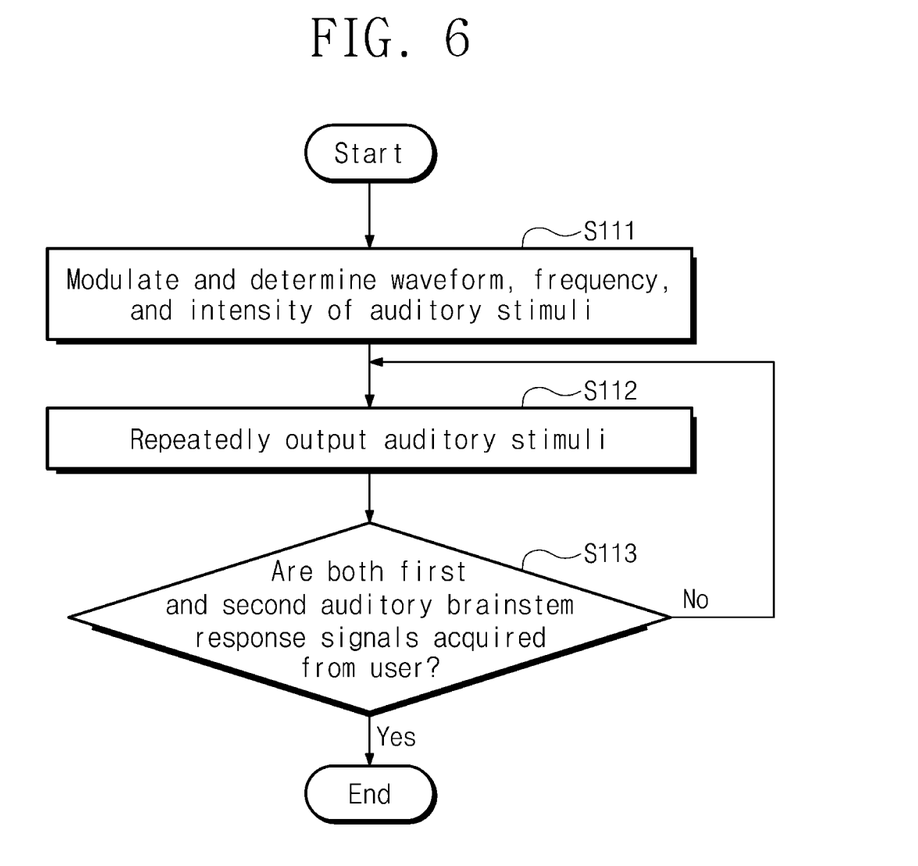
FIG. 6 illustrates a flowchart for describing detailed operations of operation S110 in FIG. 5.

FIG. 6 illustrates a flowchart for describing detailed operations of operation S110 in FIG. 5. FIG. 6 will be described in conjunction with FIGS. 1 and 5. In the following, the left side and the right side for identifying each of the ears are based on the user.

In operation S111, the signal generator 110 may modulate and determine the waveform, the frequency, and the intensity of the auditory stimuli. The modulator 111 included in the signal generator 110 may modulate and determine the waveform, the frequency, and the intensity of the auditory stimulus that are output by the first and second sound generators 20_1 and 20_2. The auditory stimulus having the waveform, the frequency, and the intensity that are determined by the modulator 111 included in the signal generator 110 may be provided to the user 10. The modulator 111 may determine the waveform of the auditory stimulus into one of various waveforms such as triangular, square, sine, pulse, click, sawtooth, ramp, chirp, tone pip, and tone burst. The frequency determined by the modulator 111 may be included in the range of the audible frequency (20 Hz to 20,000 Hz) or the range other than the audible frequency. The intensity of the auditory stimulus may be referred to as the sound intensity or the sound pressure level.

In operation S112, the signal generator 110 may repeatedly output the auditory stimuli to both ears of the user 10. The signal generator 110 may repeatedly output the auditory stimuli for the unit time. For example, the unit time may be within 1000 ms. The signal generator 110 may repeatedly output the auditory stimuli in a unit count. For example, the unit count may be 1000 or more times. The signal generator 110 may alternately output the auditory stimuli to both ears of the user 10.

In operation S113, depending on whether both the first and second auditory brainstem response signals are acquired from the user 10, the auditory stimuli may be repeatedly output to the other ear of the ears of the user 10. The first and second auditory brainstem response signals may be acquired from each of the ears of the user 10. When both the first and second auditory brainstem response signals are acquired from the user 10, the personal authentication device 100 may stop outputting the auditory stimulus.

Figure 7:
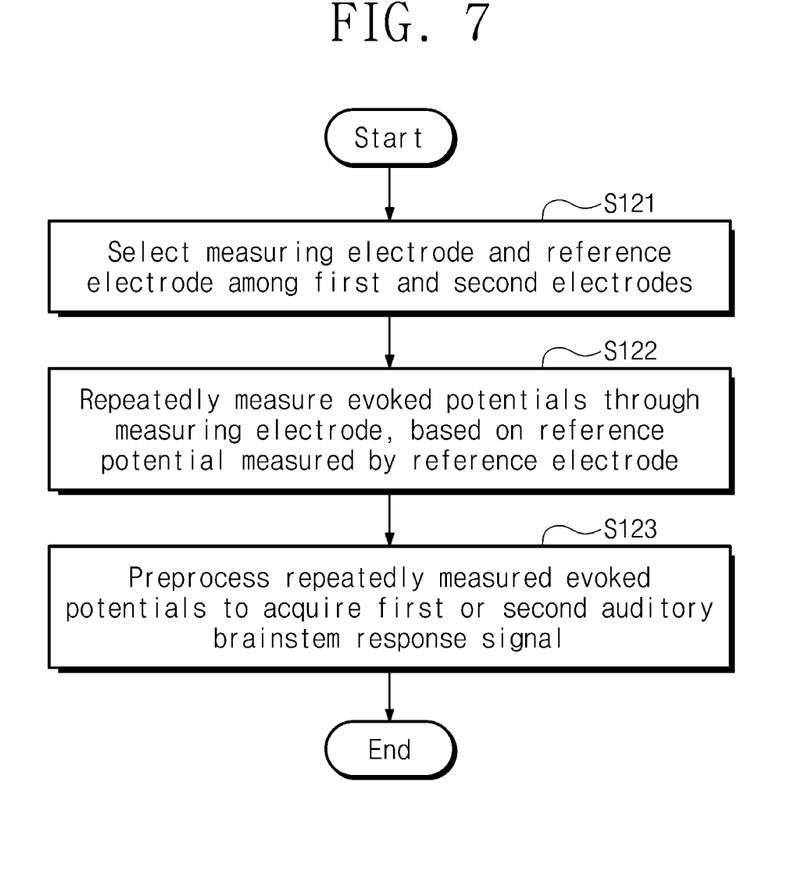
FIG. 7 illustrates a flowchart for describing detailed operations of operation S120 in FIG. 5.

FIG. 7 illustrates a flowchart for describing detailed operations of operation S120 in FIG. 5. FIG. 7 will be described with FIGS. 1 and 5.

In operation S121, the electrode selector 121 included in the signal acquirer 120 may select the measuring electrode and the reference electrode among the first and second electrodes 122_1 and 122_2. The electrode selector 121 may be synchronized with the controller 112 and may select the measuring electrode and the reference electrode, based on the selection of the controller 112.

In operation S122, the signal acquirer 120 may repeatedly acquire the evoked potentials through the measuring electrode, based on the reference potential measured by the reference electrode. The signal acquirer 120 may repeatedly acquire the evoked potential and the reference potential through the first and second electrodes 122_1 and 122_2. The signal acquirer 120 may measure the evoked potential signal from a potential difference between the first electrode 122_1 and the second electrode 122_2.

In operation S123, the signal processor 130 may preprocess the evoked potentials to generate the first or second auditory brainstem response signal. The preprocessor 131 included in the signal processor 130 may preprocess the evoked potentials to generate the first and second auditory brainstem response signals. The preprocessor 131 may take the ensemble average of the repeatedly measured evoked potentials. The auditory brainstem response signal may be generated by taking the ensemble average of the repeatedly measured evoked potentials. The preprocessor 131 may amplify the received evoked potentials. The preprocessor 131 may remove noise of the received evoked potentials. The preprocessor 131 may convert the amplified or filtered evoked potentials into digital signals. The signal processor 130 may generate the first or second auditory brainstem response signal, based on the preprocessed evoked potentials.

Figure 8:
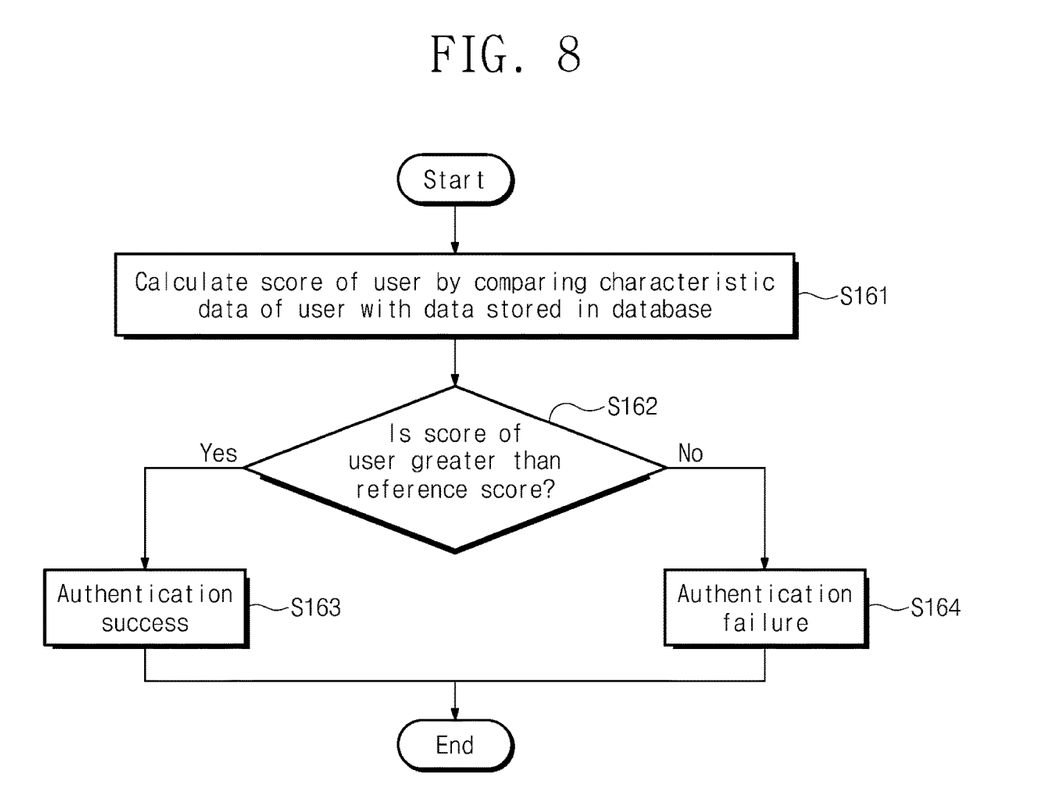
FIG. 8 illustrates a flowchart for describing detailed operations of operation S160 in FIG. 5.

FIG. 8 illustrates a flowchart for describing detailed operations of operation S160 in FIG. 5. FIG. 8 will be described with FIGS. 1 and 5.

In operation S161, the classification learner 133 may calculate the score of the user by comparing the registration data stored in the database 140 with authentication data or characteristic data of the user 10.

In operations S162, S163, and S164, the classification learner 133 may provide the authentication result to the user 10 by comparing the score of the user with the reference score. The authentication result may be provided to the user 10 as a visual signal, an audio signal, or a tactile signal.

In operation S162, the classification learner 133 may compare a size of the score of the user with a size of the reference score. When the size of the score of the user is greater than the size of the reference score, operation S163 may be proceed. Otherwise, operation S164 may proceed.

In operation S163, the personal authentication device 100 may provide a result of a successful authentication to the user 10. The personal authentication device 100 may provide or feedback the authentication result indicating the authentication success to the user 10. When the authentication is successful, the personal authentication device 100 may accept the authentication request of the user 10.

In operation S164, the personal authentication device 100 may provide the user 10 with a result that authentication is failed. An authentication result indicating the authentication failure may be provided or fed back to the user 10. When the authentication is failed, the personal authentication device 100 may reject or ignore the authentication request of the user 10.

According to embodiments of the inventive concept, a personal authentication device and a personal authentication method may enhance a security in a personal authentication and increase an accuracy of the personal authentication.

According to embodiments of the inventive concept, a personal authentication device may perform a personal authentication operation without a user's awareness and may effectively provide an authentication result to the user.

The contents described above are specific embodiments for implementing the inventive concept. The inventive concept may include not only the embodiments described above but also embodiments in which a design is simply or easily capable of being changed. In addition, the inventive concept may also include technologies easily changed to be implemented using embodiments. Therefore, the scope of the inventive concept is not limited to the described embodiments but should be defined by the claims and their equivalents.

What is claimed is:

1. A personal authentication device comprising:
   a signal generator configured to output an auditory stimulus to a first ear of a user, using a sound generator, beginning at a first time;
   a signal acquirer configured to acquire, during a first interval beginning at the first time and having a duration of 10 milliseconds:
      a first reference potential from a first electrode in close contact with a second ear of the user different from the first ear, and
      a first evoked potential from a second electrode in close contact with the first ear of the user; and
   a signal processor configured to:
      generate a first auditory brainstem response signal based on the first reference potential and the first evoked potential,
      generate authentication data for the user from the first auditory brainstem response signal, and
      compare the authentication data with registration data to authenticate the user.

2. The personal authentication device of claim 1,
   wherein the signal generator is configured to further output the auditory stimulus to the second ear of the user, using the sound generator, beginning at a second time;
   wherein the signal acquirer is further configured to acquire, during a second interval beginning at the second time, a second reference potential from the second electrode, and a second evoked potential from the first electrode of the user; and
   wherein the signal processor is further configured to generate a second auditory brainstem response signal, based on the second reference potential and the second evoked potential, and to generate the authentication data from the first and second auditory brainstem response signals.

3. The personal authentication device of claim 2,
   wherein the signal generator is configured to repeatedly output the auditory stimulus to the first ear or the second ear of the user;
   wherein the signal acquirer is configured to repeatedly acquire the first and second reference potentials and to repeatedly acquire the first and second evoked potentials; and
   wherein the signal processor is configured to calculate an average of the repeatedly acquired first and second evoked potentials, to calculate an average of the repeatedly acquired first and second reference potentials, and to generate the first and second auditory brainstem response signals, using the average of the first and second evoked potentials and the average of the first and second reference potentials.

4. The personal authentication device of claim 2,
   wherein the duration of the first interval is the same as a duration of the second interval.

5. The personal authentication device of claim 1,
   wherein the signal generator does not output the auditory stimulus to the second ear of the user when the auditory stimulus is output to the first ear of the user, and
   wherein the signal generator does not output the auditory stimulus to the first ear of the user when the auditory stimulus is output to the second ear of the user.

6. The personal authentication device of claim 1,
wherein the signal generator is configured to output a first auditory stimulus that is the auditory stimulus to the first ear of the user, based on a first condition, and further output a second auditory stimulus to the first ear of the user, based on a second condition,
wherein the signal acquirer is configured to further acquire a second reference potential corresponding to a second interval from a third time at which the second auditory stimulus is input to the first ear of the user to a fourth time, from the first electrode, and further acquire a second evoked potential corresponding to the second interval from the second electrode, based on the second reference potential, and
wherein the signal processor is configured to further generate a second auditory brainstem response signal, based on the second reference potential and the second evoked potential, and generate the authentication data from the first and second auditory brainstem response signals.

7. The personal authentication device of claim 6,
wherein the signal generator modulates a waveform, a frequency, and an intensity of the first auditory stimulus, based on the first condition, and modulates a waveform, a frequency, and an intensity of the second auditory stimulus, based on the second condition, and
wherein the first auditory stimulus is different from the second auditory stimulus.

8. The personal authentication device of claim 1,
wherein the auditory stimulus comprises at least one selected from a group consisting of a pulse waveform, a click waveform, a chirp waveform, a tone pip waveform, and a tone burst waveform.

9. The personal authentication device of claim 1, wherein the signal generator outputs the auditory stimulus to the first ear using a first earphone comprising the second electrode and inserted in the first ear, and wherein the first electrode is included in a second earphone inserted in the second ear.

10. The personal authentication device of claim 1, wherein the first electrode is positioned in contact with an inner face of an ear canal of the second ear, and
wherein the second electrode is positioned in contact with an inner face of an ear canal of the first ear.

11. The personal authentication device of claim 1, further comprising;
a database configured to store the registration data of the user, the authentication data of the user, and an authentication result for the user.

12. A personal authentication method comprising:
outputting an auditory stimulus for a registration of a user to a first ear of the user, using a sound generator;
determining a first auditory brainstem response for the user, using a first evoked potential corresponding to a first interval from a first time at which the auditory stimulus is input to the first ear of the user to a second time, from an first electrode in close contact with the first ear of the user, and a first reference potential corresponding to the first interval from a second electrode in close contact with a second ear of the user different from the first ear;
generating registration data from the first auditory brainstem response;
outputting an auditory stimulus for an authentication of the user to the first ear of the user, using the sound generator;
determining a second auditory brainstem response for the user, using a second evoked potential corresponding to a second interval from a third time at which the auditory stimulus is input to the first ear of the user to a fourth time, from the first electrode;
generating authentication data from the second auditory brainstem response; and
comparing the registration data with the authentication data to authenticate the user,
wherein the first interval and the second interval each correspond to an initial response period of 10 milliseconds.

13. The personal authentication method of claim 12, wherein the auditory stimulus for the registration of the user is the same as the auditory stimulus for the authentication of the user.

14. The personal authentication method of claim 12, wherein the authenticating of the user includes:
comparing the registration data with the authentication data; and
calculating a score of the user, based on a comparison result of the registration data and the authentication data.

15. The personal authentication method of claim 14, further comprising:
comparing the score of the user with a reference score; and
outputting an authentication result for the user, based on a result of comparing the score of the user with the reference score.

16. The personal authentication method of claim 12, further comprising generating the authentication data for the user using a second reference potential corresponding to the second interval from the second electrode.

17. The personal authentication method of claim 12, wherein the first auditory brainstem response and the second auditory brainstem response are each detected in a region of 100 to 4000 hertz.

18. The personal authentication method of claim 12, wherein the auditory stimulus for the registration of the user is at least one selected from a group consisting of a pulse waveform, a click waveform, a chirp waveform, a tone pip waveform, and a tone burst waveform.

19. The personal authentication device of claim 9, wherein the second electrode comprises a ring-shaped or looped-shape electrode disposed to surround a surface of the first earphone, and the first electrode comprises a ring-shaped or looped-shape electrode disposed to surround a surface of the second earphone.

20. The personal authentication device of claim 1, wherein the signal acquirer is configured to acquire the first evoked potential in a region of 100 to 4000 hertz.

* * * * *